United States Patent [19]

Thomalla

[11] Patent Number: 5,388,593

[45] Date of Patent: Feb. 14, 1995

[54] SURGICAL DRAPE FOR ENDOSCOPY

[75] Inventor: James V. Thomalla, Marshfield, Wis.

[73] Assignee: Marshfield Medical Research & Education Foundation, Marshfield, Wis.

[21] Appl. No.: 960,576

[22] Filed: Oct. 13, 1992

Related U.S. Application Data

[63] Continuation of Ser. No. 787,505, Nov. 4, 1991, abandoned.

[51] Int. Cl.$^6$ .......................... A61B 19/08; A61F 5/37
[52] U.S. Cl. ..................... 128/849; 128/853; 128/854
[58] Field of Search ................. 128/849, 851–856

[56] References Cited

U.S. PATENT DOCUMENTS

| | | | |
|---|---|---|---|
| 3,236,370 | 2/1966 | Pereny et al. | 128/851 |
| 3,260,260 | 7/1966 | Questel | 128/851 |
| 3,349,765 | 10/1967 | Blanford | 128/851 |
| 3,693,618 | 9/1972 | Madden | 128/855 |
| 3,878,843 | 4/1975 | Morgan | 128/851 |
| 3,882,859 | 5/1975 | Ericson | 128/854 |
| 4,080,963 | 3/1978 | Merry et al. | 128/853 |
| 4,196,723 | 4/1980 | Moose, Jr. | 128/854 |
| 4,275,719 | 6/1981 | Mayer | 128/849 X |
| 4,336,797 | 6/1982 | Latucca et al. | 128/854 |
| 4,367,728 | 1/1983 | Mutke | 128/853 X |
| 4,378,794 | 4/1983 | Collins | 128/853 |
| 4,414,568 | 11/1983 | Amin | 128/853 |
| 4,414,968 | 11/1983 | Amin | 128/853 |
| 4,462,396 | 7/1984 | Wichman | 128/853 |
| 4,570,628 | 2/1986 | Neal | 128/853 |
| 4,596,245 | 6/1986 | Morris | 128/852 |
| 4,598,458 | 7/1986 | McAllester | 128/853 |
| 4,688,563 | 8/1987 | Hanssen | 128/853 |
| 4,690,137 | 9/1987 | Starzmann | 128/849 |
| 4,807,644 | 2/1989 | Sandhaus | 128/849 |
| 4,834,068 | 5/1989 | Gottesman | 128/4 |
| 4,903,710 | 2/1990 | Jessamine et al. | 128/849 |
| 4,926,882 | 5/1990 | Lawrence | 128/853 X |
| 5,002,070 | 3/1991 | Taylor | 128/853 |

FOREIGN PATENT DOCUMENTS 93005741  4/1993  WIPO ..................... 128/849

OTHER PUBLICATIONS

Whelan, J. Paul and Birdwell Finlayson, 1991, "Decreasing the Risk of Human Immunodeficiency Virus or Hepatitis B Virus Infection During Endoscopic Surgery," *J. Urol.*, vol. 145, pp. 807–809.

Primary Examiner—Robert A. Hafer
Assistant Examiner—Brian E. Hanlon
Attorney, Agent, or Firm—Ross & Stevens

[57] ABSTRACT

A surgical drape for use by a surgeon in urological, gynecological or proctological surgical procedures or in the examination of a patient. The drape is made of a flexible visually transparent and substantially liquid impervious sheet designed to inhibit contamination to the surgeon by fluids emanating from the patient during surgical procedures. The drape includes a self-sealing aperture in the sheet, which allows access of a surgical instrument through the sheet.

4 Claims, 3 Drawing Sheets

SURGICAL DRAPE FOR ENDOSCOPY

This is a continuation of application Ser. No. 07/787,505, filed on Nov. 4, 1991, now abandoned.

FIELD OF THE INVENTION

The present invention is directed to surgical drapes, and particularly to surgical drapes for use in urological, gynecological or proctological surgical procedures, and more specifically to a surgical drape for use with an endoscope.

BACKGROUND OF THE INVENTION

For purposes of the present invention, the term "operator" is intended to encompass any of a number of practitioners specifically in the medical field including, but not limited to, urologists, doctors, nurses, technicians, surgeons, medical instrument operators and the like.

In the process of conducting certain physical examinations and surgical procedures, especially urological, gynecological or proctological procedures, close contact with the patient's genital region is required. An example of a standard surgical procedure involves the use of an endoscope. An endoscope is a urological instrument for performing tests and therapies involving the urinary tract. Basically, the endoscope is a long cylindrical instrument which traverses the urethra to diagnose a condition, i.e., by a camera or visual lens at the distal end of the endoscope, or to perform an operation. Any time an operator is using an endoscope, there is an unusually high risk of splatter contamination from fluids flowing from the patient's body. Aside from the obvious unpleasant and unhygienic conditions, the potential of body fluid contact creates a health risk to the operator.

To alleviate this concern, protective barriers have been developed to be placed between the patient and the operator. Prior art devices used to avoid contamination include wearing gloves, surgical caps, masks and goggles. Protective clothing, while helpful, provides a limited barrier because of the opportunity for fluids to pass between the articles of clothing, for example between the surgical cap and gown. Goggles tend to fog due to condensation, and the operator cannot place his eye on the ocular portion of the endoscope. Another barrier device is the use of a video camera wherein the operator can watch a video camera to the side of the patient and perform the operation. Video units, however, are expensive and unwieldy.

Yet another device on the market for preventing contamination is an endoscopic splash shield, such as that produced by Cook Urological Company and protected under U.S. Pat. No. 4,834,068 to Gottesman. A splash shield is a transparent disk approximately 12 inches in diameter with a central aperture for receiving a surgical instrument, e.g., an endoscope. While splash shields protect the operator from some contamination, their effectiveness is limited primarily because of limited size and the potential for fluid splash over and around the shield. A similar device is described and illustrated in Whelan, J. Paul and Birdwell Finlayson, 1991, "Decreasing the Risk of Human Immunodeficiency Virus or Hepatitis B Virus Infection During Endoscopic Surgery," *J. Urol.*, Vol. 145, pp. 807–809.

Another form of protection is the surgical drape. Surgical drapes are generally flexible sheets designed to drape or wrap over a patient and provide a barrier between the patient and the operator. For example, U.S. Pat. No. 4,903,710 to Jessamine et al. is directed to a surgical isolation drape for use in urological, gynecological or proctological surgical procedures. The surgical drape includes a sheet of flexible transparent or translucent plastic material. The central portion of the sheet is provided with apertures sealed by flexible members to permit passage of the surgeon's hands. The sheet can also be provided with a sealable aperture for permitting ocular access to the lens of a urological instrument. While the Jessamine et al. drape provides a patient/operator barrier, it may restrict procedures which require frequent bladder emptying. The drape also has an open top which will allow spray to pass over the drape and thus contaminate the operator's face and hands.

U.S. Pat. No. 4,596,245 to Morris describes a surgical drape for urological purposes. The drape contains a central area with a circular fenestration in the plastic drape. The fenestration is used to allow angiographic wires to be fed from the body of a patient through the fenestration when the drape is placed on the patient.

U.S. Pat. No. 4,690,137 to Starzmann discloses a surgical drape for use with urethral surgical procedures. This drape is basically a collection bowl in that it includes what is a term an annulus near the mid-portion of the drape. The apparent purpose of the annulus is to palpate the patient.

The prior art drapes, while useful to a degree, suffer a variety of deficiencies. Many simply do not prevent adequate splatter contamination control. Some, such as the Jessamine et al. invention, are complicated to operate.

BRIEF SUMMARY OF THE INVENTION

The present invention is directed to a surgical drape for use by an operator using an endoscope to probe, diagnose and treat conditions in the urinary tract. Because the endoscope has an eye piece at one end and a lens at the other end and is intended to penetrate the urethra, by necessity the operator must get close to the patient. The purpose of the surgical drape is to effectively isolate the operator from the patient's body fluids and enable the operator to examine the patient conveniently and without substantial risk of contamination.

The invention is specifically directed to a flexible, visually transparent, substantially liquid impervious sheet having the following features:

a. a first end defining a first edge, the first edge being provided with means for releasably attaching the sheet to the mid-section of the patient;

b. a second end opposite the first end, the second end defining a second edge provided with releasable attachment means, wherein the second end is configured to define a narrowed portion of the sheet such that the length of the second edge is shorter than the length of the first edge, the narrowed portion being adapted for placement between the patient's legs in such a manner that the sheet provides an effective contamination barrier between the patient and the surgeon;

c. two opposing side edges provided with means for releasably attaching the sheet to the side of the patient, wherein the side edges defining the narrowed portion of the sheet provide a non-adhesive and non-restricted access for the operator's hands for surgical manipulation; and d. a self-sealing aperture in the sheet, the aperture being adapted to allow access of a surgical instrument through the sheet.

The surgical drape of the present invention advantageously forms a contamination barrier between the operator and the patient. The drape isolates the operator from the patient's urine, rectum, blood, and irrigating fluid. This is accomplished by the continuous drape material which extends from between the patient's legs over the patient's thighs to the abdomen or abdominal drapes, and also onto the thigh or thigh drapes. The configuration forms an isolation bubble over the urethra, anus, and collection receptacle.

Further, the configuration of the drape allows plenty of room for manipulation by the operator around the sides of the drape. The sides of the drape must be opened to allow the operator's hands to be free to utilize the instrument, removing the working piece or lens, emptying the bladder, adjusting irrigation inflow, etc.

The patient's inner thighs and legs reduce splash from the sides, but the lateral splash is not as dangerous to the operator as the splash over the barrier of the drape, which would get on the lens and the surgeon's hands leading to nasal, oral or ocular facial contamination.

The isolation barrier formed by the drape of the present invention allows the operator complete mobility to even change instruments, place catheters or irrigate with freedom and still be safe from direct facial and body contamination. Hand contamination is not an issue as hands and arms are protected by surgical gloves. As such, it is important to isolate the operator's hands from the operator's face, yet allow the operator complete mobility and use of his hands. The drape of the present invention provides this environment.

The surgical drape has no limitations from the standpoint of drainage, since it does not have to contain a drain, but it is adapted to be attached to a drain.

The drape of the present invention is also flexible enough to allow the operator to move the instruments forward and backward within the urethra, which is necessary for adequate use of the instrument.

DETAILED DESCRIPTION OF THE INVENTION

Sheet

Figure 1:
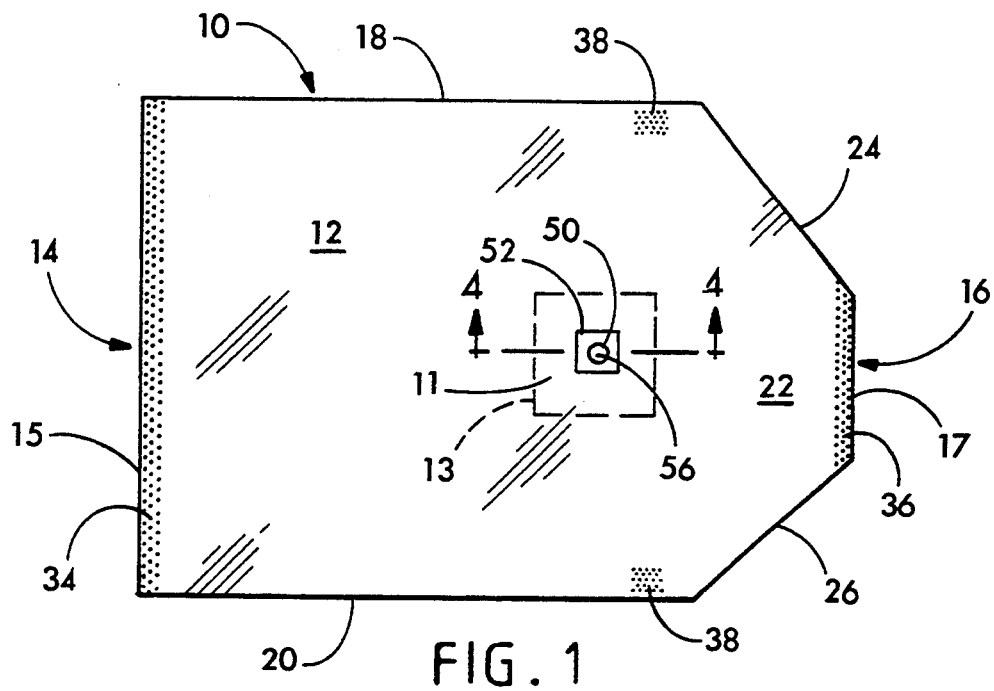
FIG. 1 is a top plan view of the surgical drape of the present invention.

Referring now to the drawings, and specifically FIG. 1, the present invention is directed to a surgical drape 10, which includes a sheet 12 of strong yet flexible plastic-like material. The sheet 12 preferably is seam-free or substantially seam-free to prevent body fluids from passing through the sheet. The drape 10 is designed to create an effective barrier between the operator and the patient. The drape 10 is generally designed in a modified rectangular shape having a first, upper end 14, a second, lower end 16 and two opposing sides 18, 20. The first end 14 includes a first edge 15, and the second end includes a second edge 17.

By necessity, at least part of the sheet 12 must be substantially transparent to allow the operator unrestricted and undistorted visual access. It is contemplated that the entire sheet 12 is substantially transparent. However, it is also within the scope of this invention to provide a limited area 11, defined by a border 13, of transparency.

Narrowed Area

Figure 2:
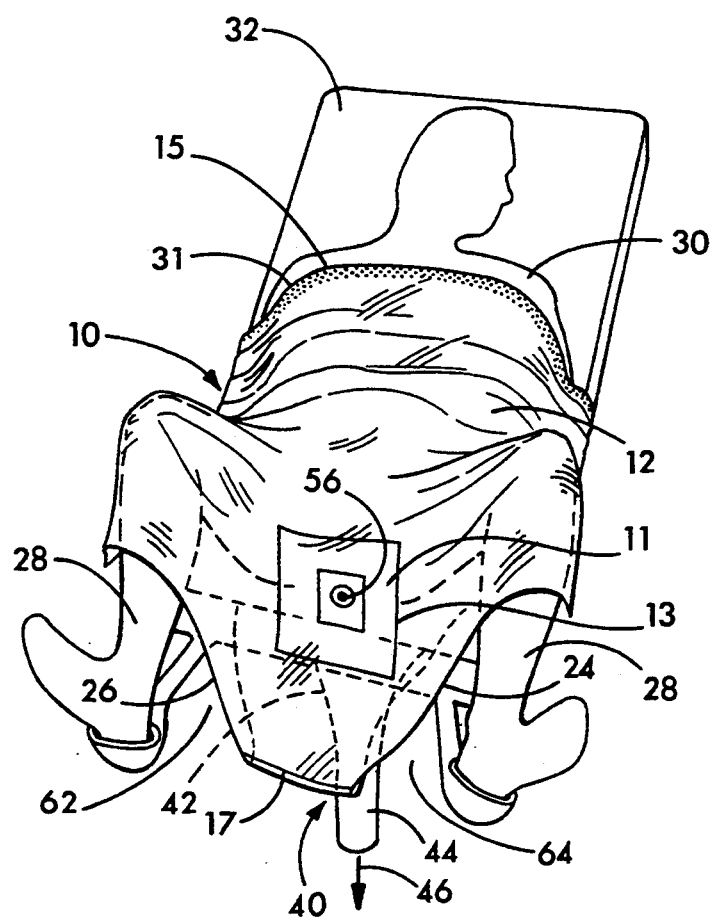
FIG. 2 is a front perspective view of the surgical drape of the present invention in place on a patient.

For ease of use, the second end 16 may include a narrowed area 22 bordered by cut-away edges 24 and 26. The cut-away edges 24, 26 are angled extensions of opposing sides 18, 20 respectively. As illustrated in FIG. 2, the narrowed area 22 is adapted for placement between the legs 28 of a patient 30 when the patient 30 assumes an examination position on a examination table 32.

Means of Attachment

First and second edges 15, 17 are provided with devices to attach the drape 10 to the patient 30, the examination table 32 or other devices according to the needs of the operator. While a variety of attachment devices are contemplated such as, for example, VELCRO® strips, ribbons, buttons, or the like, the preferred attachment devices include self-adhesive strips or tabs.

Reference is made to FIG. 1 for preferred locations of self-adhesive strips 34 and 36 and adhesive tabs 38, illustrated by stippling. While the adhesive devices are termed "strips" and "tabs," these terms do not define an exact configuration. The term "strip" is intended to imply an area of adhesion extending the length of an edge, such as edges 15 and 17. The term "tab" is intended to imply an area of adhesion having a limited length and width. For example, the size of the length and width of the adhesive tabs 38, illustrated in FIG. 1, may be between ½ inch and 2 inches.

The first adhesive strip 34 is designed to releasably attach the sheet 12 of the drape 10 to the approximate mid-section 31 of the patient 30. The mid-section 31 is intended to include the area of the patient 30 between the patient's neck and hips. Using the preferred adhesive strip 34, the sheet 12 may be equally conveniently attached to the patient's skin or a cloth covering.

Figure 3:
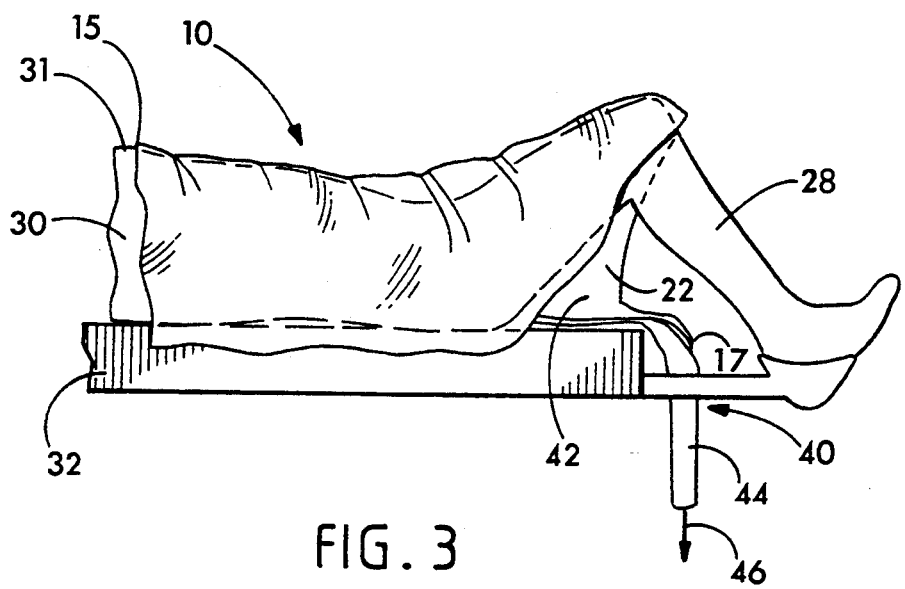
FIG. 3 is a side elevated view of the surgical drape of the present invention in place on a patient.

The second adhesive strip 36 is designed to attach the second edge 17 of the drape 10 to the examination table 32. Alternatively, the second adhesive strip 36 may be used in conjunction with a fluid receptacle 40, as illustrated in FIGS. 2 and 3. The fluid receptacle 40 is a collection repository for body and irrigation fluids flowing from the patient during examination and surgery. The receptacle 40 generally includes a drainage area 42 and a funnel 44, which directs body and irrigation fluids to a container (not shown) in the general direction of the arrow 46, illustrated in FIGS. 2 and 3. A specific example of a fluid receptacle is produced by Brant-Wald Surgicals, Inc. and illustrated in U.S. Pat. No. 4,007,741.

Figure 5:
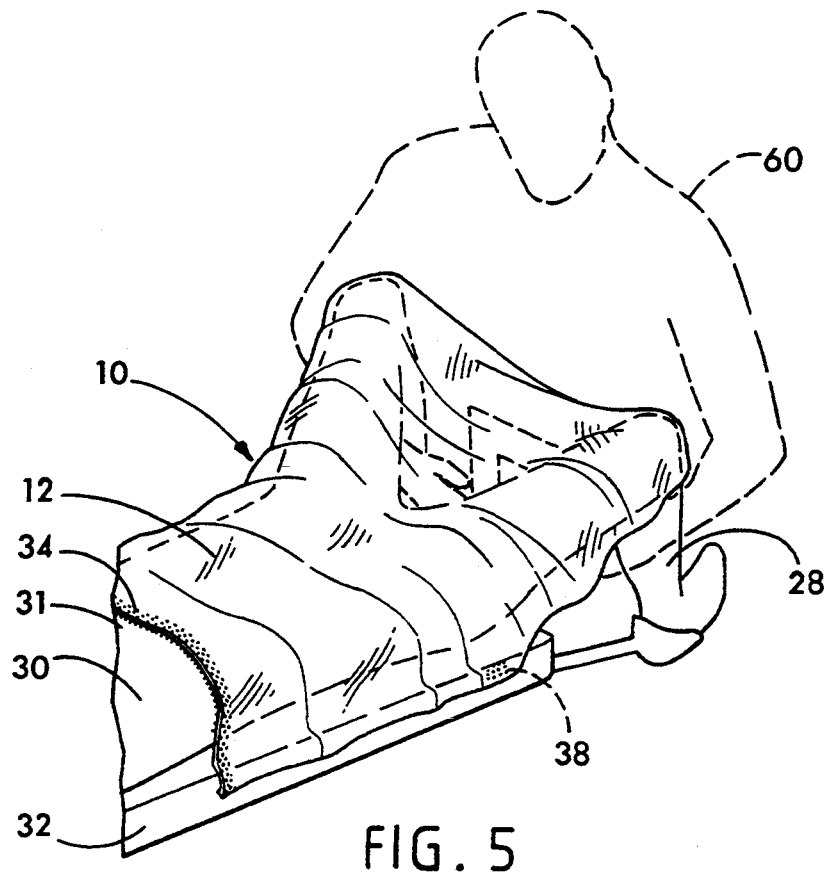
FIG. 5 is a rear perspective view of the surgical drape of the present invention in place on a patient.

Preferably, the sides 18, 20 of the drape 10 include tabs 38 of adhesive material to assist in placing and retaining the drape 10 on the patient 30 or the examination table 32 as illustrated in FIG. 5. Generally, the tabs 38 are adhesively affixed to the thighs or the thigh drapes of the patient.

Aperture

The drape 10 is also characterized by an aperture 50, which is an area generally centrally located in the narrowed area 22 of the sheet 12. The aperture 50 includes a flexible, elasticized diaphragm 52, which purpose is to allow a surgical instrument, such as an endoscope, to penetrate the drape 10, such that the operator can use the proximal or ocular end of the endoscope and still position the distal end of the endoscope in the patient's body while being protected from fluid discharge.

Figure 4:
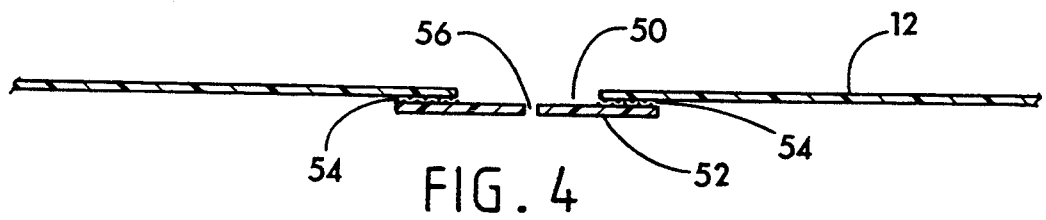
FIG. 4 is a cross-sectional view of the surgical drape of the present invention taken along line 4-4 of FIG. 1.

Referring to FIG. 4, there is illustrated a side cross-sectional view of the aperture 50, illustrating the rubberized diaphragm 52, which may be attached to the sheet 12 by an adhesive 54 in a manner known to the art. Located centrally in the aperture portion diaphragm 52 is a diaphragm opening 56, which purpose is to allow the endoscope or other operating instrument to pass through the drape 10, while still protecting the operator. Because of the elastic quality of the diaphragm 52, the opening 56 forms a slidable yet substantially sealed passage for the endoscope. Thus, body fluids will not likely pass through the sheet 12 at the area of the diaphragm 52.

Manner of Using Drape

Referring now to FIGS. 2, 3, 5 and 6, there are illustrated various positions of the patient 30 showing the drape 10 in use. The patient 30 is placed upon an examination table 32 for examination by an operator 60. The drape 10 is attached at its first edge 15 at or around the mid-section 31 of the patient 30. The adhesive strip 34 may be attached directly to the patient's body or to a mid-section drape (not illustrated). Side tabs 38 are then attached to the patient's leg 28 or examination table 32 near the area of the patient's thigh, thus securing the drape to the patient 30. The second edge 17 of the drape 10 is preferably attached to a fluid receptacle 40 as illustrated in FIGS. 2 and 3.

Figure 6:
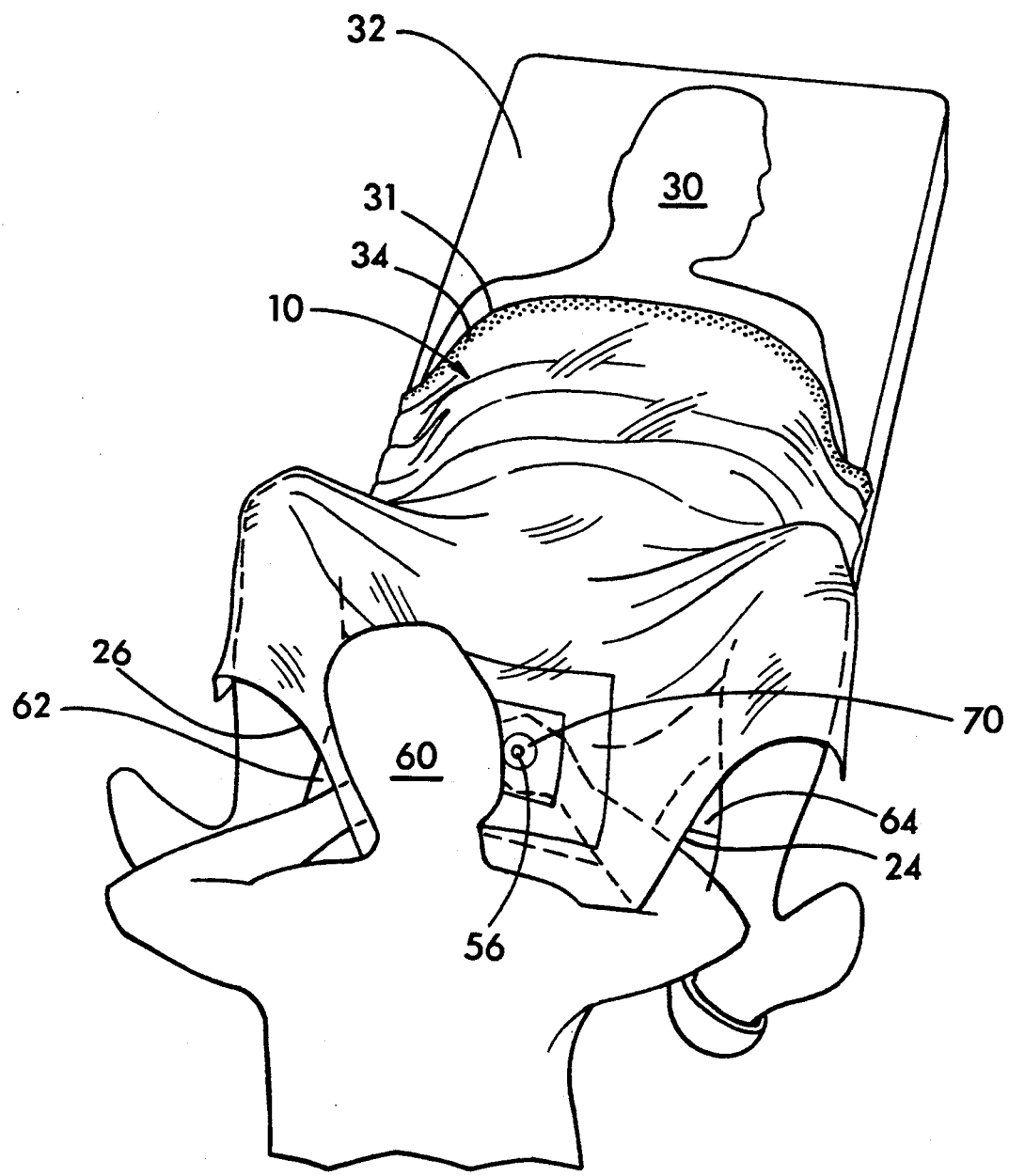
FIG. 6 is a front perspective view illustrating an endoscope operator in use.

When the drape 10 is in place on the patient 30, as illustrated in FIG. 5, the operator 60 is then protected from fluid contamination during an examination or surgical procedure. The operator 60 is positioned, as illustrated in FIGS. 5 and 6, and, due to the transparency of the sheet 12, has unfettered visual access to the patient 30. The operator 60 may position an endoscope 70 through the diaphragm opening 56 and manipulate the endoscope with his hands via access channels 62, 64 formed between the legs 28 of the patient 30 and the cut-away edges 24, 26, respectively of the drape 10.

It is understood that the invention is not confined to the particular construction and arrangement herein illustrated and described, but embraces such modified forms thereof as come within the scope of the following claims.

What is claimed is:

1. A surgical drape for use in endoscopic procedures, comprising a protective barrier between the surgeon and the patient, the barrier allowing the surgeon to conduct surgical manipulation of an endoscopic instrument on the patient while protecting the surgeon from patient fluid contamination, the barrier comprising a flexible visually transparent substantially liquid impervious sheet having a first end, a second end, and first and second opposing sides, the sheet consisting essentially of:

a. a first edge at the first end, the first edge being provided with adhesive means along the entire first edge between the first and second opposing sides for releasably sealing the entire first edge to the patient and forming a protective seal between the sheet and the patient at the first edge, the protective seal providing a protective barrier between the patient and the surgeon;

b. an isolation barrier at the second end of the sheet, the second end defining a first, cut-away edge, a second, distal edge and a third, cut-away edge between the opposing first and second sides, wherein the first, cut-away edge extends inwardly at approximately a 45 degree angle from the first side toward the second, distal edge and the third, cut-away edge extends inwardly at approximately a 45 degree angle from the second side toward the second, distal edge, wherein the second, distal edge is located between the first and third, cut-away edges thereby forming a shape substantially equivalent to a bottom half of a hexagon, and wherein the length of each of the first, cut-away, second, distal and third, cut-away edges is shorter in length than the first edge of the first end thereby defining a narrowed portion of the sheet, the narrowed portion being adapted for placement between the patient's legs such that the first and third, cut-away edges of the second end are positioned over the patient's legs and the second, distal edge of the second end is placed between the patient's legs thereby providing an effective isolation barrier between the surgeon and the patient;

c. means for releasably attaching the first and second sides of the sheet to the patient;

d. adhesive means along the second edge of the second end of the sheet; and e. a friction-fit, self-sealing aperture in the sheet, the aperture being adapted to allow access of a surgical instrument through the sheet and to prevent fluid contamination leakage.

2. The surgical drape of claim 1 wherein the adhesive means for releasably sealing the first edge of the first end of the sheet to the patient comprises self-sealing strips.

3. The surgical drape of claim 1 wherein the adhesive means along the second edge of the second end comprises self-adhesive strips.

4. The surgical drape of claim 1 wherein the means for releasably attaching the first and second sides of the sheet to the patient comprises self-adhesive tabs attached to the first and second sides of the sheet.

* * * * *